US008598395B2

(12) United States Patent
Negiz et al.

(10) Patent No.: US 8,598,395 B2
(45) Date of Patent: *Dec. 3, 2013

(54) PROCESS FOR INCREASING A MOLE RATIO OF METHYL TO PHENYL

(75) Inventors: Antoine Negiz, Wilmette, IL (US); Edwin Paul Boldingh, Arlington Heights, IL (US); Gregory J. Gajda, Mt. Prospect, IL (US); Dean E. Rende, Arlington Heights, IL (US); James E. Rekoske, Glenview, IL (US); David E. Mackowiak, Mt. Prospect, IL (US); Paul Barger, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 38 days.

This patent is subject to a terminal disclaimer.

(21) Appl. No.: 12/689,560

(22) Filed: Jan. 19, 2010

(65) Prior Publication Data

US 2011/0178356 A1    Jul. 21, 2011

(51) Int. Cl.
*C07C 2/66*    (2006.01)
(52) U.S. Cl.
USPC .......................................... 585/467; 585/446
(58) Field of Classification Search
USPC ................................................. 585/446, 467
See application file for complete search history.

(56) References Cited

U.S. PATENT DOCUMENTS

| | | | |
|---|---|---|---|
| 2,168,590 A * | 8/1939 | Taylor | 585/470 |
| 3,751,506 A | 8/1973 | Burress | |
| 3,965,207 A | 6/1976 | Weinstein | |
| 4,283,584 A | 8/1981 | Chester et al. | |
| 4,491,678 A | 1/1985 | Oda et al. | |
| 4,899,008 A | 2/1990 | LaPierre | |
| 4,899,012 A | 2/1990 | Sachtler et al. | |
| 4,975,179 A | 12/1990 | Harandi et al. | |
| 5,434,326 A | 7/1995 | Gajda | |
| 5,665,223 A | 9/1997 | Bogdan | |
| 5,847,256 A | 12/1998 | Ichioka et al. | |
| 5,900,520 A | 5/1999 | Mazzone et al. | |
| 5,935,417 A | 8/1999 | Cody et al. | |
| 6,099,719 A | 8/2000 | Cody et al. | |
| 6,867,339 B2 | 3/2005 | Kong et al. | |
| 7,005,058 B1 | 2/2006 | Towler | |
| 7,081,556 B2 | 7/2006 | Buchanan et al. | |
| 7,169,368 B1 | 1/2007 | Sullivan et al. | |
| 7,179,434 B1 | 2/2007 | Maher et al. | |
| 7,314,601 B2 | 1/2008 | Negiz et al. | |
| 7,396,967 B2 | 7/2008 | Iaccino et al. | |
| 7,439,412 B2 | 10/2008 | Ou et al. | |
| 7,453,018 B2 | 11/2008 | Dakka | |
| 7,456,124 B2 | 11/2008 | Boldingh et al. | |
| 7,601,311 B2 | 10/2009 | Casey et al. | |
| 7,615,197 B2 | 11/2009 | Negiz et al. | |
| 7,655,823 B2 | 2/2010 | Mohr | |
| 2003/0028059 A1 | 2/2003 | Hamper | |
| 2004/0030210 A1 | 2/2004 | Mohr | |
| 2008/0051615 A1 | 2/2008 | Stavens et al. | |
| 2008/0058564 A1 | 3/2008 | Iaccino | |
| 2009/0036724 A1 | 2/2009 | Negiz et al. | |
| 2009/0047190 A1 | 2/2009 | Zhou | |

FOREIGN PATENT DOCUMENTS

| | | |
|---|---|---|
| EP | 1 201 730 A1 | 5/2002 |
| RU | 2 144 942 C1 | 1/2000 |
| WO | WO-00/50366 | 8/2000 |

OTHER PUBLICATIONS

Abstract of Chen et al., Developmental Trends in p-Xylene Production Increasing Technology, Petrochemical Technology, 2004, vol. 33, No. 10, 1 Page.
Abstract of Sidorenko et al., Selective Alkylation of Methyl-Substituted Aromatic Hydrocarbons over Acidic and Basic Zeolites, Neftekhimiya, Jan.-Feb. 1991, vol. 31, No. 1, 1 Page.
Ali et al., Development of Nanoporous Structured Catalysts for Xylenes Production, King Fand University of Petroleum and Minerals, Research Institute—Annual Catalysts in Petroleum Refining and Petrochemicals Symposium Papers 2007, 2007, pp. 121-129.
Commissaris, UOP Parex Process, Handbook of Petroleum Refining Processes, 2004, vol. 3rd Ed., pp. 2.47-2.54.
D'Aquino, Technology: Novel Zeolite Catalysts, Chemical Engineering Progress, Jun. 2002, vol. 98, No. 6, p. 14.
Das et al., Aromatization of C4-C6 Hydrocarbons to Benzene, Toluene and Para Xylene over Pore Size Controlled ZnO-HZSM-5 Zeolite, Catalysis Society of India 13th National Symposium & Silver Jubilee Symposium, 1998, vol. 113, pp. 447-453.
Jeanneret et al., New Strategies Maximize Para-Xylene Production, Hydrocarbon Processing, Jun. 1994, vol. 74, No. 6, pp. 43-45, 47-49.
Johnson, Aromatics Complexes, Handbook of Petroleum Refining Processes, 2004, vol. 3rd Ed., p. 2.3-2.11.
Kim et al., Para-Selectivity of Zeolites with MFI Structure . . . Difference Between Disproportionation and Alkylation, Applied Catalysis A: General, 1992, vol. 83, No. 1, pp. 51-58.
Negiz et al., UOP Tatoray Process, Handbook of Petroleum Refining Processes, 2004, vol. 3rd Ed., pp. 2.55-2.63.
Peterson et al., Q-MaxTM Process for Cumene Production, Handbook of Petroleum Refining Processes, 2004, vol. 3rd Ed., pp. 1.69-1.77.
Silady, UOP Isomar Process, Handbook of Petroleum Refining Processes, 2004, vol. 3rd Ed., pp. 2.39-2.46.
Speight, The Chemistry and Technology of Petroleum, CRC Press, 2007, 4th Ed., p. 446.
Stoodt et al., UOP Sulfolane Process, Handbook of Petroleum Refining Processes, 2004, vol. 3rd Ed., pp. 2.13-2.23.
Stoodt et al., UOP Thermal Hydrodealkylation (THDA) Process, Handbook of Petroleum Refining Processes, 2004, vol. 3rd Ed., pp. 2.25-2.28.
UOP Inc, LPG Anchors an Economic New Process to Make Para-Xylene, Chemical Engineering, Apr. 27, 1987, vol. 94, No. 6, p. 9.

(Continued)

*Primary Examiner* — Thuan D Dang
(74) *Attorney, Agent, or Firm* — Mark R Willis

(57) ABSTRACT

One exemplary embodiment can be a process for increasing a mole ratio of methyl to phenyl of one or more aromatic compounds in a feed. The process can include reacting an effective amount of one or more aromatic compounds and an effective amount of one or more aromatic methylating agents to form a product having a mole ratio of methyl to phenyl of at least about 0.1:1 greater than the feed.

14 Claims, No Drawings

(56) References Cited

OTHER PUBLICATIONS

U.S. Appl. No. 12/176,290, entitled Process and Apparatus for Producing a Gasoline, by James et al., Filed Jul. 18, 2008.
U.S. Appl. No. 12/179,524, entitled Process and Apparatus for Producing a Reformate by Introducing Isopentane, by Krupa et al., Filed Jul. 24, 2008.
U.S. Appl. No. 12/179,542, entitled Process and Apparatus for Producing a Reformate by Introducing n-Butane, by Krupa et al., Filed Jul. 24, 2008.
U.S. Appl. No. 12/179,552, entitled Process and Apparatus for Producing a Reformate by Introducing Methane, by Krupa et al., Filed Jul. 24, 2008.
U.S. Appl. No. 12/689,630, entitled Process for Increasing Methyl to Phenyl Mole Ratios and Reducing Benzene Content in a Motor Fuel Product, by Negiz et al., Filed Jan. 19, 2010.
U.S. Appl. No. 12/689,751, entitled an Aromatic Aklylating Agent and an Aromatic Production Apparatus, by Negiz et al., Filed Jan. 19, 2010.
Zhou, BP-UOP Cyclar Process, Handbook of Petroleum Refining Processes, 2004, vol. 3rd Ed., pp. 2.29-2.37.
Miale, Catalysis by Crystalline Aluminosilicates, Journal of Catalysis, vol. 6, 1966, pp. 278-287.
Nace, Catalytic Cracking Over Crystalline Aluminosilicates, I & EC Product Research and Development, vol. 8, No. 1, Mar. 1969, pp. 31-38.
Morikawa, The Activation of Specific Bonds in Complex Molecules at Catalytic Surfaces. I. The Carbon-Hydrogen Bond in Methane and Methane-d4, Journal A. Chem. Soc. 58, Aug. 1936, pp. 1445-1449.
Taylor, The Hydrogenation of Ethane on Cobalt Catalysts, Journal A. Chem. Soc., vol. 61, Feb. 1939, pp. 503-509.
Joris, The Catalytic Interaction of Hydrogen and Deuterium with Ethylene and Deuteroethylenes on Copper, Journal A. Chem. Soc., vol. 60, Aug. 1938, pp. 1982-1986.
Sinfelt, Hydrogenolysis of Ethane Over Supported Platinum, Journal of Physical Chemistry, vol. 68, No. 2, Feb. 1964, pp. 344-346.

\* cited by examiner

PROCESS FOR INCREASING A MOLE RATIO OF METHYL TO PHENYL

FIELD OF THE INVENTION

This invention generally relates to a process for increasing a mole ratio of methyl to phenyl of, e.g., one or more aromatic compounds.

DESCRIPTION OF THE RELATED ART

Typically, an aromatic complex can process a hydrotreated naphtha feed to produce various products, such as benzene and one or more xylenes. However, it may be desirable to produce higher substituted aromatics, depending, e.g., on market conditions. In addition, when producing motor fuel products, increasingly stringent environmental regulations can require lower benzene content. As a consequence, there is a demand for alternative processes for removing benzene from, e.g., gasoline. Thus, systems and processes that allow flexibility to convert benzene to other and higher valued products may be desirable.

However, existing processes can use expensive catalysts and/or reactants that can require further processing to separate undesirable side products. Thus, it would be advantageous to provide an agent that can convert benzene to other substituted aromatics while minimizing undesirable products and/or side reactions.

SUMMARY OF THE INVENTION

One exemplary embodiment can be a process for increasing a mole ratio of methyl to phenyl of one or more aromatic compounds in a feed. The process can include reacting an effective amount of one or more aromatic compounds and an effective amount of one or more aromatic methylating agents to form a product having a mole ratio of methyl to phenyl of at least about 0.1:1 greater than the feed.

Another exemplary embodiment may be a process for reacting one or more aromatic compounds in a feed. The process may include reacting the feed including an effective amount of one or more aromatic compounds and an effective amount of one or more aromatic methylating agents to obtain a product having an aromatic ring recovery of about 85-about 115%, by mole, with respect to the feed and having a mole ratio of methyl to phenyl of at least about 0.1:1 greater than the feed.

Yet another exemplary embodiment can be a process for increasing a mole ratio of methyl to phenyl of one or more aromatic compounds in a feed. The process can include providing one or more aromatic methylating agents from a stream to a reaction zone adapted to receive the one or more aromatic methylating agents to form at least one $A7^+$ compound by increasing the mole ratio of methyl to phenyl of at least about 0.1:1 greater than the feed.

The embodiments disclosed herein can provide a process for increasing the mole ratio of methyl to phenyl of one or more aromatic compounds. As a consequence, the process disclosed herein can convert aromatics to higher substituted compounds. Such converted compounds can be higher valued, depending on market conditions, such as para-xylene. Thus, the value of the products produced by the aromatic complex may be increased. Moreover, the embodiments disclosed herein can remove undesired amounts of compounds, such as benzene, from a product, such as a motor fuel product.

In addition, an aromatic alkylating or methylating agent utilized can be one or more non-aromatic compounds or radicals that may be present in the feed of the naphtha and can be provided from one or more fractionation towers within the aromatic complex. Thus, the non-aromatic compounds, such as alkanes or cycloalkanes, may be easily combined with the one or more aromatics to produce higher substituted compounds. In addition, typically less desired compounds such as cumene, indane, and other higher substituted aromatics may also be utilized so that their saturated radicals can alkylate or methylate aromatics, such as benzene, to produce more desired products, such as xylenes. Preferably, the process creates additional substituent methyl groups on the one or more aromatic compounds. Thus, the embodiments disclosed herein can provide an economical and relatively simple system for converting benzene in an aromatic complex.

Definitions

As used herein, the term "stream", "feed", or "product" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 ... Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8 ... An where "n" represents the number of carbon atoms in the one or more aromatic molecules. Furthermore, a superscript "+" or "−" may be used with an abbreviated one or more hydrocarbons notation, e.g., $C3^+$ or $C3^-$, which is inclusive of the abbreviated one or more hydrocarbons. As an example, the abbreviation "$C3^+$" means one or more hydrocarbon molecules of three or more carbon atoms.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "aromatic alkylating agent" means a non-aromatic compound or radical used to produce higher alkyl substituted one or more aromatic compounds. Examples of one or more non-aromatic compounds can include an alkane or a cycloalkane, preferably at least one C2-C8 alkane or $C5^+$ cycloalkane. A non-aromatic radical can mean a saturated group forming a linear or branched alkyl group, a cycloalkyl, or a saturated group fused to an aromatic ring. Aromatic compounds having such non-aromatic radicals can include cumene, indane, and tetralin. The alkylated aromatic compounds can include additional substituent groups, such as methyl, ethyl, propyl, and higher groups. Generally, an aromatic alkylating agent includes atoms of carbon and hydrogen and excludes hetero-atoms such as oxygen, nitrogen, sulfur, phosphorus, fluorine, chlorine, and bromine.

As used herein, the term "aromatic methylating agent" means a non-aromatic compound or radical used to produce higher methyl substituted one or more aromatic compounds. Examples of one or more non-aromatic compounds can include an alkane or a cycloalkane, preferably at least one C2-C8 alkane or $C5^+$ cycloalkane. A non-aromatic radical can mean a saturated group forming a linear or branched alkyl group, a cycloalkyl, or a saturated group fused to an aromatic ring. Aromatic compounds having such non-aromatic radicals can include cumene, indane, and tetralin. The methylated aromatic compounds can include additional substituent methyl groups. Generally, an aromatic methylating agent includes atoms of carbon and hydrogen and excludes heteroatoms such as oxygen, nitrogen, sulfur, phosphorus, fluorine, chlorine, bromine, and iodine. Such hetero-atom compounds may be referred to as a "methylating agent" and may include compounds such as iodomethane, dimethyl sulfate, dimethyl carbonate, and methyl trifluorosulfonate.

As used herein, the term "radical" means a part or a group of a compound. As such, exemplary radicals can include methyl, ethyl, cyclopropyl, cyclobutyl, and fused ring-roups to an aromatic ring or rings.

As used herein, the term "rich" can mean an amount of at least generally about 50%, and preferably about 70%, by mole, of a compound or class of compounds in a stream.

As used herein, the term "substantially" can mean an amount of at least generally about 80%, preferably about 90%, and optimally about 99%, by mole, of a compound or class of compounds in a stream.

As used herein, the term "metal" can include rhenium, tin, germanium, lead, indium, gallium, zinc, uranium, dysprosium, thallium, chromium, molybdenum, tungsten, iron, cobalt, nickel, platinum, palladium, rhodium, ruthenium, osmium, or iridium.

As used herein, the methyl to phenyl ratio can be calculated as follows:

$$\text{Methyl:Phenyl Mole Ratio} = [\text{Total number of methyls}]/[\text{Total Aromatic Rings}]$$

Where: Total Aromatic Rings=sum over all i ($MS(i)/MW(i)*NR(i)$)

Total Number of Methyls=sum over all i ($MS(i)/MW(i)*ME(i)$)

i: Compound Species

Molecular weight for species i: $MW(i)$

Number of aromatic (phenyl) rings for species i: $NR(i)$

Number of methyl groups attached onto the phenyl rings of species i: $ME(i)$

The mass content of species i, in the feed: $MS(i)$

Exemplary calculations for various compound species are depicted below:

Single ring aromatics: i: Toluene, $NR(i)=1$, $ME(i)=1$; i: Xylene, $NR(i)=1$, $ME(i)=2$ Fused aromatic rings: i: Indane, $NR(i)=1$, $ME(i)=0$; i: Tetralin, $NR(i)=1$, $ME(i)=0$;

i: Naphthalene, $NR(i)=2$, $ME(i)=0$

Substituents on saturated fused ring: i: 1-methyl-indane and 2-methyl-indane (where one methyl group is attached to the five carbon ring), $NR(i)=1$, $ME(i)=0$ Substituents on unsaturated fused ring: i: 4-methyl-indane and 5-methyl-indane (where one methyl group is attached to the phenyl ring), $NR(i)=1$, $ME(i)=1$; i: dimethyl 2,6-naphthalene, $NR(i)=2$, $ME(i)=2$ Hence, methyl groups are counted when attached to an aromatic group, e.g., phenyl, and not counted when attached to a full or partial, e.g., fused, saturated ring for fused-ring compounds having aromatic and saturated rings.

As used herein, the percent, by mole, of the aromatic ring recovery with respect to the feed can be calculated as follows:

$$\text{Aromatic Ring Recovery} = [\text{Total Aromatic Rings, By Mole, of Product}]/[\text{Total Aromatic Rings, By Mole, of Feed}]*100\%$$

As used herein, the conversion percent, by weight, of $C6^+$ non-aromatic compounds from the feed can be calculated as follows:

$$\text{Conversion} = (((\text{Total Mass Feed } C6^+ \text{ non-aromatics}) - (\text{Total Mass Product } C6^+ \text{ non-aromatics}))/(\text{Total Mass Feed } C6^+ \text{ non-aromatics}))*100\%$$

DETAILED DESCRIPTION

The embodiments provided herein can provide a product having a mole ratio of alkyl, preferably methyl, to phenyl greater than the feed. Particularly, a feed, which may include one or more $C8^-$ hydrocarbons, can be provided to a reaction zone that may increase the methyl substituents on an aromatic ring. Usually, the feed can be provided from one source or multiple sources and include an effective amount of one or more aromatic compounds and one or more non-aromatic compounds absent heteroatoms or aromatic compounds with saturated groups, i.e., one or more aromatic alkylating or methylating agents. Generally, the feed can come from a variety of sources, such as products of reforming, hydrotreating, catalytic or non-catalytic cracking, such as pygas, oligomerizing, condensating, hydroprocessing, coking, vacuum and non-vacuum hydrocarbon distilling, aromatics separating including extracting, and any combination thereof. In addition, at least one of a liquefied petroleum gas, a reformate obtained from cracking, and raffinate from an aromatics extraction zone may be used, alone or in combination, with at least one feed from the sources described above. The non-aromatic compounds and saturated groups can act as an aromatic alkylating, preferably methylating, agent to increase the number of alkyl, preferably methyl, groups on the aromatic compounds. Although one benefit provided by the embodiments discussed herein is increasing the number of methyl groups, it should also be understood that the number of alkyl groups may also be increased as well. Hence, an aromatic methylating agent may also act as an aromatic alkylating agent.

The non-aromatic compounds can include at least one of, independently, one or more cycloalkanes and alkanes, and may comprise at least about 5%, by weight, of the feed. Optionally, the one or more non-aromatic compounds may also include one or more olefins. Usually, the non-aromatic compound includes at least two, preferably three, and even more preferably four carbon atoms and can include at least one of a cycloalkane, which preferably has at least three, desirably five, carbon atoms in the ring, and, independently, a C2-C8 alkane. In other preferred embodiments, the non-aromatic compounds can include one or more $C6^+$ non-aromatic compounds. In yet another preferred embodiment, the one or more $C6^+$ non-aromatic compounds can include at least one of a dimethyl cyclopentane and a methyl cyclopentane. The feed may include at least about 10%, by weight, one or more cycloalkanes, or about 10-about 70%, by weight, one or more cycloalkanes with respect to the weight of the feed. Moreover, the feed may include up to about 50%, by weight, of one or more C2-C5 hydrocarbons with respect to the weight of the feed.

Typically, the feed can include aromatic compounds, such as $A6^+$, well. The aromatic compounds can include benzene, toluene, one or more xylenes, naphthalene, ethylbenzene, and one or more polynuclear aromatics. The feed can also include naphthalene rings or multiple fused aromatic rings such as polynuclear aromatics (hereinafter may be abbreviated "PNA").

In addition, the aromatic compounds may also include saturated groups. Such compounds may include cumene, indane, and tetralin. As discussed above, the saturated groups may act as an alkylating, preferably methylating, agent.

With respect to the feed, the feed generally includes about 20%, preferably about 35%, by weight, one or more aromatics. In addition, the feed may include about 5%, by weight, benzene with the balance being non-aromatics and with a maximum amount of about 5%, by weight, toluene. In order to obtain a product that can be rich in xylenes, the preferred benzene content in the feed is less than about 75%, by weight, with respect to the weight of the feed. To obtain a product rich in toluene, the benzene content in the feed may be greater than about 75%, by weight, with respect to the weight of the feed. In another embodiment, the feed generally includes at least about 5%, by weight, toluene and at least about 5%, by weight, benzene with a balance of non-aromatics based on the weight of the feed. In yet another preferred embodiment, the feed generally includes benzene in an amount of about 0.5-about 99.5%, by weight, toluene in the amount of about 0.5-about 99.5%, by weight, and non-aromatics in the amount of about 0.5-about 99.5%, by weight, based on the weight of the feed. In yet other embodiments, the feed can include at least about 20%, by weight, benzene with respect to the weight of the feed.

Typically, the feed can comprise about 20-about 95%, by weight, of one or more aromatics, such as benzene, with respect to the weight of the feed. In some other embodiments, the benzene content of the feed can be about 15-about 25%, by weight, with respect to the weight of the feed.

Usually, the feed is substantially absent of methylating agents containing one or more hetero-atoms. As an example, the feed can have less than about 1%, preferably less than about 0.1%, by weight, of one or more methylating agents. Instead, the feed can include an aromatic alkylating agent of one or more saturated compounds or radicals in an amount of at least about 5%, by mole, based on the feed.

The reaction zone, such as an alkyl, preferably methyl, addition zone can operate under any suitable conditions in the liquid or gas phase. Particularly, the reaction zone can operate at a temperature of about 250-about 700° C, preferably about 350-about 550° C., a pressure of about 100-about 21,000 kPa, preferably about 1,900-about 3,500 kPa, a weight hourly space velocity (WHSV) of about 0.1-about 100 $hr^{-1}$, preferably about 2-about 10 $hr^{-1}$, and a hydrogen:hydrocarbon mole ratio of about 0.1:1-about 5:1, preferably about 0.5:1-about 4:1. In another exemplary embodiment, the temperature can be at least about 460° C., desirably at least about 510° C., and more desirably at least about 560° C., a pressure no more than about 7,000 kPa, preferably no more than about 3,500 kPa, and the reaction may occur in a gas phase to facilitate the cracking of non-aromatic hydrocarbons. Alternatively, the temperature can be about 460-about 550° C. At higher temperature and lower pressure conditions, although not wanting to be bound by theory, it is believed that the non-aromatic hydrocarbons and/or saturated groups will form methyl groups instead of alkyl groups. However, it should be understood that at least some alkylation may be occurring where groups such as, e.g. ethyl, propyl, butyl, and higher groups, can be substituted to the one or more aromatic compounds.

Any suitable catalyst may be utilized such as at least one molecular sieve including any suitable material, e.g., alumino-silicate. The catalyst can include an effective amount of the molecular sieve, which can be a zeolite with at least one pore having a 10 or higher member ring structure and can have one or higher dimension. Typically, the zeolite can have a $Si/Al_2$ mole ratio of greater than about 10:1, preferably about 20:1-about 60:1. Preferred molecular sieves can include BEA, MTW, FAU (including zeolite Y in both cubic and hexagonal forms, and zeolite X), MOR, LTL, ITH, ITW, MEL, FER, TON, MFS, IWW, MFI, EUO, MTT, HEU, CHA, ERI, MWW, and LTA. Preferably, the zeolite can be MFI and/or MTW. Suitable zeolite amounts in the catalyst may range from about 1-about 99%, and preferably from about 10-about 90%, by weight. The balance of the catalyst can be composed of a refractory binder or matrix that is optionally utilized to facilitate fabrication, provide strength, and reduce costs. Suitable binders can include inorganic oxides, such as at least one of alumina, magnesia, zirconia, chromia, titania, boria, thoria, phosphate, zinc oxide and silica.

Generally, the catalyst is essentially absent of at least one metal, and typically includes less than about 0.1%, by weight, of total metal based on the weight of the catalyst. Moreover, the catalyst preferably has less than about 0.01%, more preferably has less than about 0.001%, and optimally has less than about 0.0001%, by weight, of total metal based on the weight of the catalyst.

The product produced from the reaction zone can have a mole ratio of methyl to phenyl groups of at least about 0.1:1, preferably greater than about 0.2:1, and optimally greater than about 0.5:1, greater than the feed. The reaction zone can produce an aromatic ring recovery of generally at least about 85%, preferably about 85-about 115%, and optimally about 99-about 101%, by mole, with respect to the feed. Generally, the conversion of one or more $C6^+$ non-aromatic compounds can be greater than about 50%, preferably greater than about 70%, and optimally greater than about 90%, by weight. Thus, the reaction of the one or more $C6^+$ non-aromatic compounds as well as the benzene can minimize the amount of benzene in the resulting product. Typically, the aromatic compounds can receive one or more methyl groups, and optionally other alkyl groups, such as ethyl, propyl, or higher carbon chain substituents.

The product can include one or more $A7^+$ compounds, such as toluene, one or more xylenes, and ethylbenzene. As such, the product may include at least generally about 2% xylenes, preferably about 5%, and optimally about 10%, by weight, of one or more xylenes. In addition, the para-xylene percent of the total xylenes can be at least about 20%, preferably at least about 23%, and optimally at least about 23.8%. In other preferred embodiments, the feed can include at least 0.5%, by weight, benzene with respect to the weight of the feed and produce a product that has less than about 0.5%, by weight, benzene with respect to the weight of the product. In yet other preferred embodiments, the feed can contain greater than about 0.5%, by weight, benzene with respect to the weight of the feed and have a product that is less than about 20%, by weight, benzene with respect to the weight of the product. In still other preferred embodiments, the benzene content in the product can be reduced to less than about 20%, by weight, and preferably less than about 0.5%, by weight, with respect to the weight of the product. Any benzene that is present in the feed can be substituted with a saturated group present in one or more other aromatic compounds, such as polynuclear aromatics, in order to obtain a product that may be rich in methyl group substituted aromatics, including substituted one or more naphthalenes and other polynuclear aromatics.

What is more, the reaction zone can convert other compounds, such as one or more olefin compounds, one or more sulfur-containing compounds and one or more halide-containing compounds. Particularly, about 80%, by weight, of the one or more $C3^+$ olefins can be converted with respect to the feed. Preferably, sulfur-containing compounds, such as thiophene and thiophene derivatives, one or more $C3^+$ mercaptans, as well as one or more heavier halides can be converted by at least about 95%, by weight, with respect to the feed. In addition, other compounds may also be converted such as one or more oxygen-containing compounds, e.g., one or more tertiary butyl alcohol compounds.

Generally, a downstream process can utilize one or more products, such as benzene, para-xylene, meta-xylene and ortho-xylene, of the embodiments disclosed herein. Particularly, para-xylene, upon oxidation, can yield terephthalic acid used in the manufacture of textiles, fibers, and resins. Moreover, para-xylene can be used as a cleaning agent for steel and silicon wafers and chips, a pesticide, a thinner for paint, and in paints and varnishes. Meta-xylene can be used as an intermediate to manufacture plasticizers, azo dyes, wood preservatives and other such products. Ortho-xylene can be a feedstock for phthalic anhydride production. Additionally, xylenes generally may be used as a solvent in the printer, rubber, and leather industries. Moreover, the methyl groups on xylenes can be chlorinated for use as lacquer thinners. Benzene can be used as a feed to make cyclohexane, which in turn may be used to make nylons. Also, benzene can be used as an intermediate to make styrene, ethylbenzene, cumene, and cyclohexane. Moreover, smaller amounts of benzene can be used to make one or more rubbers, lubricants, dyes, detergents, drugs, explosives, napalm, and pesticides.

EXAMPLES

The following examples are intended to further illustrate the subject embodiments. These illustrations of embodiments of the invention are not meant to limit the claims of this invention to the particular details of these examples. These examples are based on engineering calculations and actual operating experience with similar processes.

All three runs are simulated at generally the same conditions, such as at a pressure of about 2,760 kPa, except a first run is at a temperature of 481.4° C., a second run is at a temperature of 511.3° C., and a third run at a temperature of 568.5° C. The composition in percent, by weight, of the feed and product runs as well as the results are depicted in Table 1 below:

TABLE 1

|  | FEED | PRODUCT RUN 1 | PRODUCT RUN 2 | PRODUCT RUN 3 |
|---|---|---|---|---|
| C1 | 0.00 | 7.8 | 14.9 | 24.6 |
| C2 | 0.00 | 10.8 | 17.5 | 23.0 |
| C3 | 0.12 | 16.1 | 9.9 | 2.3 |
| n-C4 | 0.21 | 1.9 | 0.6 | 0.2 |
| i-C4 | 0.90 | 1.9 | 0.8 | 0.2 |
| n-C5 | 5.43 | 1.0 | 0.0 | 0.0 |
| i-C5 | 5.96 | 1.7 | 0.2 | 0.0 |
| C6-C8 non-aromatics | 36.89 | 4.4 | 0.9 | 0.4 |
| XY | 0.03 | 4.2 | 6.1 | 5.4 |
| TOL | 0.98 | 14.6 | 19.4 | 18.3 |
| EB | 0.00 | 3.9 | 2.5 | 1.2 |
| BZ | 49.03 | 27.5 | 22.5 | 19.7 |
| A9+ | 0.44 | 4.3 | 4.6 | 4.6 |
| TOTAL | 100.00 | 100.0 | 100.0 | 100.0 |
| Methyl:phenyl mole ratio | 0.02 | 0.4 | 0.6 | 0.6 |
| Benzene conversion % | 0.00 | 44.0 | 54.1 | 59.8 |
| C5 non-aromatic conversion % | 0.00 | 76.9 | 98.4 | 99.8 |
| Average Rx Temp ° C. | 0.00 | 481.4 | 511.3 | 568.5 |
| C6-C8 non-aromatic conversion % | 0.00 | 88.2 | 97.5 | 99.1 |

As depicted, each product for each run can have a methyl: phenyl mole ratio of at least about 0.1:1 greater than the feed, while the products of runs 2 and 3 at an average reaction temperature of at least 511° C. exceed a conversion of 90% for C6-C8 non-aromatics.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for increasing a mole ratio of methyl to phenyl of one or more aromatic hydrocarbon compounds in a feed, comprising:
   reacting an effective amount of one or more aromatic hydrocarbon compounds and an effective amount of one or more aromatic methylating agents having at least three carbon atoms comprising at least one of an alkane, a cycloalkane, an alkane radical, and a cycloalkane radical in the presence of a catalyst comprising one or more catalysts selected from MTW, MOR, and MFI molecular sieves, an alumina binder, and absent metals to form a product having a mole ratio of methyl to phenyl of at least about 0.1:1 greater than the feed.

2. The process according to claim 1, wherein the one or more aromatic methylating agents comprises at least one of a cycloalkane and a C3-C8 alkane.

3. The process according to claim 1, wherein the one or more aromatic hydrocarbon compounds comprises benzene.

4. The process according to claim 1, wherein the feed comprises at least about 5%, by weight, of benzene with respect to the weight of the feed.

5. The process according to claim 1, wherein the feed comprises at least about 10%, by weight, of one or more cycloalkanes with respect to the weight of the feed.

6. The process according to claim 1, wherein the catalyst comprises at least one of an MFI and MTW zeolite.

7. The process according to claim 1, wherein the one or more aromatic methylating agents comprises at least one of a cycloalkane and a C5-C8 alkane.

8. The process according to claim 1, wherein the one or more aromatic methylating agents comprises at least one cycloalkane.

9. The process according to claim 1, wherein the product has a mole ratio of methyl to phenyl of at least about 0.2:1 greater than the feed.

10. A process for reacting one or more aromatic hydrocarbon compounds in a feed, comprising:
    reacting the feed comprising an effective amount of one or more aromatic hydrocarbon compounds and an effective amount of one or more aromatic methylating agents having at least three carbon atoms comprising at least one of an alkane, a cycloalkane, an alkane radical, and a cycloalkane radical in the presence of a catalyst comprising one or more zeolites selected from MTW, MOR, and MFI, an alumina binder and absent metal to obtain a product having an aromatic ring recovery of about 85-about 115%, by mole, with respect to the feed and having a mole ratio of methyl to phenyl of at least about 0.1:1 greater than the feed.

11. The process according to claim 10, wherein the feed comprises at least about 5%, by weight, of benzene with respect to the weight of the feed.

12. The process according to claim 10, wherein the one or more aromatic methylating agents comprises at least one cycloalkane.

13. A process for increasing a mole ratio of methyl to phenyl of one or more aromatic hydrocarbon compounds in a feed, comprising:
   providing one or more aromatic methylating agents having at least three carbon atoms comprising at least one of an alkane, a cycloalkane, an alkane radical, and a cycloalkane radical from a stream to a reaction zone in the presence of a catalyst comprising a molecular sieve comprising one or more of MTW, MOR, and MFI, an alumina binder, and absent metal, and adapted to receive the one or more aromatic methylating agents to form at least one $A7^+$ compound comprising ethylbenzene by increasing the mole ratio of methyl to phenyl of at least about 0.1:1 greater than the feed.

14. The process according to claim 13, wherein the one or more aromatic methylating agents comprises at least one of a cycloalkane and a C3-C8 alkane.

\* \* \* \* \*